United States Patent [19]

Smith

[11] 4,211,713

[45] Jul. 8, 1980

[54] AROMATIC ANALOGS OF 4,5,13,14-TETRADEHYDRO-PGI$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 915,347

[22] Filed: Jun. 14, 1978

Related U.S. Application Data

[63] Continuation-in-part of Ser. No. 821,536, Aug. 3, 1977.

[51] Int. Cl.$^2$ .............................................. C07D 307/93
[52] U.S. Cl. ........................... 260/346.73; 260/346.22; 542/426

[58] Field of Search .................... 260/346.22, 346.73; 542/426

[56] References Cited

PUBLICATIONS

Fried et al., Proc. Natl. Acad. Sci. 74, 2199 (1977).

*Primary Examiner*—Henry R. Jiles
*Assistant Examiner*—Bernard Dentz
*Attorney, Agent, or Firm*—Robert A. Armitage

[57] ABSTRACT

The present invention relates to certain structural and pharmacological analogs of prostacyclin (PGI$_2$) which are aromatic analogs of 4,5,13,14-tetradehydro-PGI$_1$ compounds. These novel pharmacological agents are useful as smooth muscle stimulators.

43 Claims, No Drawings

AROMATIC ANALOGS OF 4,5,13,14-TETRADEHYDRO-PGI₁ COMPOUNDS

CROSS REFERENCE TO RELATED APPLICATION

The present application is a continuation-in-part application of Ser. No. 821,536, filed Aug. 3, 1977, now pending issuance as a United States Patent.

The present invention relates to prostacyclin analogs, for which the essential material constituting disclosure therefor is incorporated by reference here from Ser. No. 821,541, filed Aug. 3, 1977, now U.S. Pat. No. 4,109,082, issued Aug. 22, 1978.

I claim:

1. A prostacyclin analog of the formula

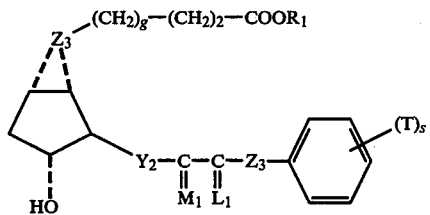

wherein $Y_2$ is —C≡C—;
wherein $Z_2$ is

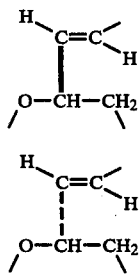

wherein g is the integer zero, one, or 2;
wherein $M_1$ is

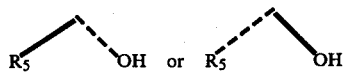

wherein $R_5$ is hydrogen or alkyl with one to 4 carbon atoms, inclusive,
wherein $L_1$ is

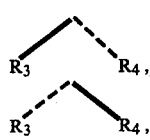

or a mixture of

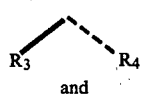

and

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

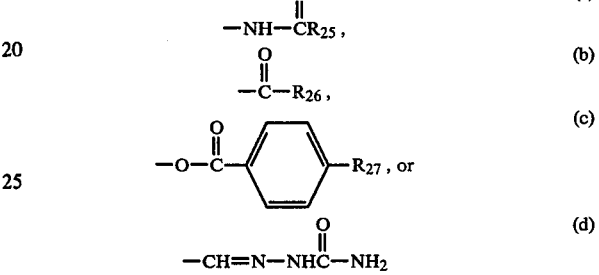

wherein $R_{25}$ is methyl, phenyl, acetamidophenyl, benzamidophenyl, or —NH₂; $R_{26}$ is methyl, phenyl, —NH₂, or methoxy; and $R_{27}$ is hydrogen or acetamido; inclusive, i.e.,

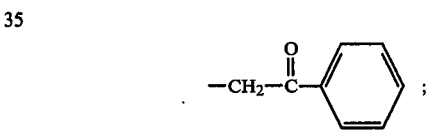

phenacyl substituted in the para position by chloro, bromo, phenyl, or benazmido; or a pharmacologically acceptable cation; and
wherein $Z_3$ is oxa or —(CH₂)ₕ—,
wherein h is the integer zero to 3, inclusive;
wherein s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Z_3$ is oxa.

3. A prostacyclin analog according to claim 2, wherein $Z_2$ is a mixture of

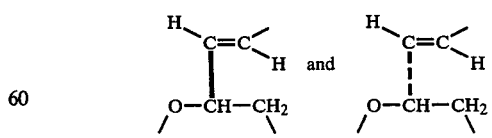

4. trans-4,5,13,14-Tetradehydro-(6RS)-16-phenoxy-17,18,19,20-tetranor-PGI₁, a prostacyclin analog according to claim 3.

5. A prostacyclin analog according to claim 2, wherein $Z_2$ is

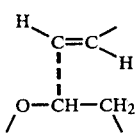

6. trans-4,5,13,14-Tetradehydro-16-phenoxy-17,18,19,20-tetranor-6α-PGI$_1$, a prostacyclin analog according to claim 5.

7. 15-Methyl-trans-4,5,13,14-tetradehydro-16-phenoxy-17,18,19,20-tetranor-6α-PGI$_1$, a prostacyclin analog according to claim 5.

8. 16-Methyl-trans-4,5,13,14-tetradehydro-16-phenoxy-18,19,20-trinor-6α-PGI$_1$, a prostacyclin analog according to claim 5.

9. 16,16-Difluoro-trans-4,5,13,14-tetradehydro-16-phenoxy-17,18,19,20-tetranor-6α-PGI$_1$, a prostacyclin analog according to claim 5.

10. A prostacyclin analog according to claim 2, wherein $Z_2$ is

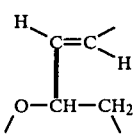

11. A prostacyclin analog according to claim 10, wherein $R_5$ is methyl.

12. 15-Methyl-trans-4,5,13,14-tetradehydro-16-phenoxy-17,18,19,20-tetranor-6β-PGI$_1$, a prostacyclin analog according to claim 11.

13. A prostacyclin analog according to claim 10, wherein $R_5$ is hydrogen.

14. A prostacyclin analog according to claim 13, wherein at least one of $R_3$ and $R_4$ is fluoro.

15. 16,16-Difluoro-trans-4,5,13,14-tetradehydro-16-phenoxy-17,18,19,20-tetranor-6β-PGI-$_1$, a prostacyclin analog according to claim 14.

16. A prostacyclin analog according to claim 13, wherein at least one of $R_3$ and $R_4$ is methyl.

17. 16-methyl-trans-4,5,13,14-tetradehydro-16-phenoxy-18,19,20-trinor-6β-PGI$_1$, a prostacyclin analog according to claim 16.

18. A prostacyclin analog according to claim 13, wherein $R_3$ and $R_4$ are both hydrogen.

19. trans-4,5,13,14-Tetradehydro-16-phenoxy-17,18,19,20-tetranor-6β-PGI$_1$, methyl ester, a prostacyclin analog according to claim 18.

20. trans-4,5,13,14-Tetradehydro-16-phenoxy-17,18,19,20-tetranor-6β-PGI$_1$, tris(hydroxymethyl)amino methane salt, a prostacyclin analog according to claim 18.

21. trans-4,5,13,14-Tetradehydro-16-phenoxy-17,18,19,20-tetranor-6β-PGI$_1$, adamantanamine salt, a prostacyclin analog according to claim 18.

22. trans-4,5,13,14-Tetradehydro-16-phenoxy-17,18,19,20-tetranor-6β-PGI$_1$, a prostacyclin analog according to claim 18.

23. A prostacyclin analog according to claim 1, wherein $Z_3$ is —(CH$_2$)$_h$—.

24. A prostacyclin analog according to claim 23, wherein $Z_2$ is a mixture of

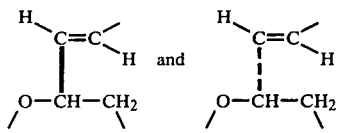

25. trans-4,5,13,14-Tetradehydro-(6RS)-17-phenyl-18,19,20-trinor-6α-PGI$_1$, a prostacyclin analog according to claim 24.

26. A prostacyclin analog according to claim 23, wherein $Z_2$ is

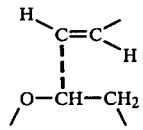

27. trans-4,5,13,14-Tetradehydro-17-phenyl-18,19,20-trinor-6α PGI$_1$, a prostacyclin analog according to claim 26.

28. 15-Methyl-trans-4,5,13,14-tetradehydro-17-phenyl-18,19,20-trinor-6α-PGI$_1$, a prostacyclin analog according to claim 26.

29. 16,16-Dimethyl-trans-4,5,13,14-tetradehydro-17-phenyl-18,19,20-trinor-6α-PGI$_1$, a prostacyclin analog according to claim 26.

30. 16,16-Difluoro-trans-4,5,13,14-tetradehydro-17-phenyl-18,19,20-trinor-6α-PGI$_1$, a prostacyclin analog according to claim 26.

31. A prostacyclin analog according to claim 23, wherein $Z_2$ is

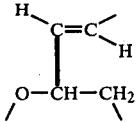

32. A prostacyclin analog according to claim 31, wherein $R_5$ is methyl.

33. 15-Methyl-trans-4,5,13,14-tetradehydro-17-phenyl-18,19,20-trinor-6β-PGI$_1$, a prostacyclin analog according to claim 32.

34. A prostacyclin analog according to claim 31, wherein $R_5$ is hydrogen.

35. A prostacyclin analog according to claim 34, wherein at least one of $R_3$ and $R_4$ is fluoro.

36. 16,16-Difluoro-trans-4,5,13,14-tetradehydro-17-phenyl-18,19,20-trinor-6β-PGI$_1$, a prostacyclin analog according to claim 35.

37. A prostacyclin analog according to claim 34, wherein at least one of $R_3$ and $R_4$ is methyl.

38. 16,16-Dimethyl-trans-4,5,13,14-tetradehydro-17-phenyl-18,19,20-trinor-6β-PGI$_1$, a prostacyclin analog according to claim 37.

39. A prostacyclin analog according to claim 34, wherein $R_3$ and $R_4$ are both hydrogen.

40. trans-4,5,13,14-Tetradehydro-17-phenyl-18,19,20-trinor-6β-PGI$_1$, methyl ester, a prostacyclin analog according to claim 39.

41. trans-4,5,13,14-Tetradehydro-17-phenyl-18,19,20-trinor-6β-PGI$_1$, tris(hydroxymethyl)amino methane salt, a prostacyclin analog according to claim 39.

42. trans-4,5,13,14-Tetradehydro-17-phenyl-18,19,20-trinor-6β-PGI$_1$, adamantanamine salt, a prostacyclin analog according to claim 39.

43. trans-4,5,13,14-Tetradehydro-17-phenyl-18,19,20-trinor-6β-PGI$_1$, a prostacyclin analog according to claim 39.

* * * * *

UNITED STATES PATENT OFFICE
CERTIFICATE OF CORRECTION

Patent No. 4,211,713          Dated 8 July 1980

Inventor(s) Herman W. Smith

It is certified that error appears in the above-identified patent and that said Letters Patent are hereby corrected as shown below:

Column 1, lines 20-25, that portion of the formula reading

   should read   

Signed and Sealed this

Seventh Day of April 1981

[SEAL]

Attest:

RENE D. TEGTMEYER

Attesting Officer     Acting Commissioner of Patents and Trademarks